US010420861B2

(12) United States Patent
Jeong et al.

(10) Patent No.: US 10,420,861 B2
(45) Date of Patent: Sep. 24, 2019

(54) NANOFIBER MATS, METHOD OF MANUFACTURING THE NANOFIBER MATS, AND APPLICATIONS TO CELL CULTURE AND NANOFIBROUS MEMBRANE FOR GUIDED BONE REGENERATION

(71) Applicant: ST1 Co., LTD, Busan (KR)

(72) Inventors: Young Hun Jeong, Daegu (KR); Jong-young Kwak, Busan (KR); Jeong Hwa Kim, Jeollabuk-do (KR); Chang Gun Kim, Busan (KR)

(73) Assignee: ST1 CO., LTD., Busan (KR)

( * ) Notice: Subject to any disclaimer, the term of this patent is extended or adjusted under 35 U.S.C. 154(b) by 317 days.

(21) Appl. No.: 15/028,322

(22) PCT Filed: Jun. 26, 2015

(86) PCT No.: PCT/KR2015/006573
§ 371 (c)(1),
(2) Date: Apr. 8, 2016

(87) PCT Pub. No.: WO2015/199492
PCT Pub. Date: Dec. 30, 2015

(65) Prior Publication Data
US 2016/0250393 A1 Sep. 1, 2016

(30) Foreign Application Priority Data

Jun. 27, 2014 (KR) .................. 10-2014-0079596
Jun. 30, 2014 (KR) .................. 10-2014-0080422

(51) Int. Cl.
*A61L 31/12* (2006.01)
*A61L 27/38* (2006.01)
(Continued)

(52) U.S. Cl.
CPC ............. *A61L 31/125* (2013.01); *A61L 27/18* (2013.01); *A61L 27/3821* (2013.01);
(Continued)

(58) Field of Classification Search
CPC .... A61L 31/125; A61L 27/3821; A61L 27/18; A61L 31/146; A61L 31/16; A61L 27/56;
(Continued)

(56) References Cited

U.S. PATENT DOCUMENTS

2014/0081414 A1\* 3/2014 Hall .................. A61L 27/16
623/23.7

FOREIGN PATENT DOCUMENTS

KR 100736840 7/2007
KR 10-0875189 12/2008
(Continued)

OTHER PUBLICATIONS

English Translation of KR 2009-0117140, Kim et al, A three dimensional hybrid scaffold by bioplotting and electrospinning system, 2009, pp. 1-6. (Year: 2009).\*
(Continued)

*Primary Examiner* — Trevor Love
(74) *Attorney, Agent, or Firm* — Norton Rose Fulbright US LLP

(57) ABSTRACT

Disclosed are a nanofiber mat, a manufacturing method thereof, and applications thereof as a mat for cell culturing or as a barrier membrane for guided bone regeneration (GBR). The nanofiber layer includes a nanofiber layer and a reinforcement pattern that is disposed on the nanofiber layer and adhesively connected with the nanofiber layer. The nanofiber layer and the reinforcement pattern are combined with each other by at least one of the melting-solidification of at least a part of the nanofiber layer together with the reinforcement pattern, the dissolution-solidification of the
(Continued)

same, and the penetration of a part of the reinforcement pattern into the nanofiber layer, followed by solidification.

11 Claims, 6 Drawing Sheets

(51) Int. Cl.
    *A61L 27/18*     (2006.01)
    *C12M 1/12*     (2006.01)
    *C12N 5/00*     (2006.01)
    *A61L 31/14*     (2006.01)
    *A61L 31/16*     (2006.01)
    *C12N 5/077*     (2010.01)
    *A61L 27/56*     (2006.01)
    *A61L 27/54*     (2006.01)

(52) U.S. Cl.
    CPC .............. *A61L 27/54* (2013.01); *A61L 27/56* (2013.01); *A61L 31/146* (2013.01); *A61L 31/16* (2013.01); *C12M 25/14* (2013.01); *C12N 5/0068* (2013.01); *C12N 5/0654* (2013.01); *A61L 2400/12* (2013.01); *A61L 2430/02* (2013.01); *C12N 2533/30* (2013.01); *C12N 2535/10* (2013.01); *C12N 2537/00* (2013.01)

(58) Field of Classification Search
    CPC .. A61L 27/54; A61L 2430/02; A61L 2400/12; C12M 25/14; C12N 5/0068; C12N 5/0654; C12N 2535/10; C12N 2537/00; C12N 2533/30
    See application file for complete search history.

(56) References Cited

FOREIGN PATENT DOCUMENTS

| | | |
|---|---|---|
| KR | 1020090117140 | 11/2009 |
| KR | 1020100126095 | 12/2010 |
| KR | 101377558 | 3/2014 |

OTHER PUBLICATIONS

English Translation of KR 20090117140. (Year: 2009).*
International Search Report and Written Opinion issued in PCT/KR2015/006573, dated Sep. 14, 2015.

* cited by examiner

NANOFIBER MATS, METHOD OF MANUFACTURING THE NANOFIBER MATS, AND APPLICATIONS TO CELL CULTURE AND NANOFIBROUS MEMBRANE FOR GUIDED BONE REGENERATION

CROSS-REFERENCE TO RELATED APPLICATIONS

This application is a national phase application under 35 U.S.C. § 371 of International Application No. PCT/KR2015/006573 filed 26 Jun. 2015, which claims priority to Korean Patent Applications No. 10-2014-0079596 filed 27 Jun. 2014 and No. 10-2014-0080422 filed 30 Jun. 2014. The entire contents of each of the above-referenced disclosures is specifically incorporated herein by reference.

TECHNICAL FIELD

The present invention relates to a nanofiber mat, a manufacturing method thereof, and applications thereof as a mat for cell culturing or as a barrier membrane for guided bone regeneration (GBR), and, more particularly, to a nanofiber mat with an ease of handling, a manufacturing method thereof, and applications thereof as a mat for cell culturing or as a barrier membrane for GBR.

BACKGROUND ART

In recent years, much attention has been paid to nanofibers, and they have been subjects of great interest in an aspect pertaining to cell culturing. In particular, fibers produced by electrospinning are fibers with a very small diameter, and they are advantageous in that they have a very large surface area per unit volume, are flexible, highly porous, and a large number of fibers are present per unit area, thus being capable of blending with other material(s) and exhibiting large distribution of an external stress. In a biomedical field, nanofiber aggregates (e.g. nanofiber mats) having a morphologically similar structure to the extracellular matrix of a human body are used as substrates for cell culturing, and mats that can be used by being placed in a cell culture dish (petri-dish) were commercialized and are being sold to serve a purpose of generally using nanofibers for cell culturing.

However, nanofiber mats are highly flexible, and thus handling thereof is not easy and there is much limitation to maintaining an evenly spread shape inside a dish. Therefore, they are initially fabricated into a form of an attachment to a cell culture dish or prepared with a very large thickness, and thus it is difficult to use them in various ways during an experiment, and they have various problems such as an increased cost and limited range of application.

In the meantime, barrier membranes used in guided bone regeneration (GBR) are materials that prevent a defective area of an osseous tissue from being exposed to a fibrous connective tissue, prevent bacteria from entering, and provide a site for bone regeneration. The barrier membranes are used in alveolar bone regeneration, the treatment of defects or the regeneration of other types of bones in various areas of a human body. Recently, the barrier membranes have been developed to perform additional functions as well as bone regeneration by containing additional bioactive factors. Depending on constituent materials, barrier membranes can be roughly categorized into inorganic barrier membranes, which consist of inorganic substances such as titanium, and polymer barrier membranes. The polymer barrier membranes can be categorized into being resorbable and non-resorbable, depending on whether they are absorbed in a human body or not.

Inorganic barrier membranes have advantages such as high rigidity and high structural stability, but they are highly incompatible with a human tissue. Non-resorbable polymer barrier membranes have relatively higher biocompatibility in comparison to inorganic barrier membranes and have relatively higher rigidity and structural stability in comparison to resorbable polymer barrier membranes. However, both inorganic barrier membranes and non-resorbable polymer barrier membranes have disadvantages in that they need to be kept continuously in a human body even after the recovery of defective tissues or require an additional surgery for the removal thereof.

In contrast, resorbable polymer barrier membranes are advantageous in that they have high biocompatibility, can perform a variety of functions such as shielding, drug-releasing, and the like, and do not require separate removal. Nevertheless, nanofiber-based resorbable polymer barrier membranes have a form of a nonwoven fabric by an electrospinning or freeze-drying process, and thus their rigidity value is very low. Resorbable polymer barrier membranes with low rigidity have limitations in that they are difficult to handle at a time of a procedure, enough space in a human body cannot be provided for the long term, and applying them to a heavily loaded part is challenging.

DISCLOSURE

Technical Problem

Hence, technical tasks of the present invention were conceived in this respect. The present invention is directed to providing a nanofiber mat with the ease of introduction of various types of directional flexibility and rigidity, and a manufacturing method thereof.

The present invention is also directed to providing a nanofiber mat that is suitable for cell culturing.

Further, the present invention is directed to providing a barrier membrane for guided bone regeneration (GBR) that is highly biologically reactive and is based on a resorbable polymer.

Technical Solution

According to one exemplary embodiment for accomplishing one of the above objects of the present invention, a nanofiber mat includes a nanofiber layer and a reinforcement pattern that is disposed on the nanofiber layer and connected with the nanofiber layer. The nanofiber layer and the reinforcement pattern are combined with each other by at least one of the melting-solidification of at least a part of the nanofiber layer together with the reinforcement pattern, the dissolution-solidification of the same, and the penetration of a part of the reinforcement pattern into the nanofiber layer, followed by solidification.

In one exemplary embodiment, any one of the nanofiber layer and the reinforcement pattern may contain at least one of biologically reactive substances, magnetic materials, and carbon nano tube or particles.

In one exemplary embodiment, the shape of the reinforcement pattern may be any one selected among a square lattice, a circular lattice, a rhombic lattice, a zigzag, a line, and a curve or various combinations of them.

In one exemplary embodiment, the nanofiber layer may have a structure in which nanofibers are randomly arranged, aligned along one direction, arranged in two directions, where one direction intersects the other, or combined them.

In one exemplary embodiment, the reinforcement pattern may fill between a surface, on which the reinforcement pattern of the nanofiber layer is formed, and a back surface at least partially so that the migration of a material is restricted by the reinforcement pattern.

In one exemplary embodiment, the reinforcement pattern is formed in a central area of the nanofiber layer and improves rigidity of the central area, and a peripheral area of the above nanofiber layer, which surrounds the central area, is a region where the reinforcement pattern is not formed and may have flexibility due to the nanofiber layer.

In one exemplary embodiment, the reinforcement pattern includes at least 2 subpatterns having mutually different shapes, and the rigidity of regions in which the subpatterns are formed may be mutually different. In this case, shapes of the subpatterns may be at least one selected from a square lattice, a circular lattice, a rhombic lattice, a zigzag, a line, and a curve.

In one exemplary embodiment, the reinforcement pattern has a curved shape with a spiral structure. When a torque is applied along the axial direction of the spiral structure, the nanofiber layer may contract (i.e. the radius of the structure can reduce), and when the torque is removed, the contracted nanofiber layer may be relaxed and at least partially restored.

In one exemplary embodiment, the nanofiber mat may be a nanofiber mat for cell culturing.

In one exemplary embodiment, the nanofiber mat may be a barrier membrane for GBR.

A method of manufacturing a nanofiber mat according to the present invention includes a process of preparing a nanofiber layer, and a process of forming a reinforcement pattern by printing, on the nanofiber layer, a polymer resin in a state of a polymer melt or a polymer solution.

In one exemplary embodiment, during the process of forming a reinforcement pattern, at least a part of the nanofiber layer may be melted by the polymer melt or polymer solution, and the nanofiber layer that was at least partially melted may solidify together with the polymer melt or polymer solution to form the reinforcement pattern.

In one exemplary embodiment, in the process of forming a reinforcement pattern, a fused deposition modeling (FDM) device may be used.

In one exemplary embodiment, in the process of forming a reinforcement pattern, the solution or the melt may penetrate into the nanofiber layer and solidify together with the nanofiber layer.

Advantageous Effects

According to such a nanofiber mat, a manufacturing method thereof, and applications thereof as a mat for cell culturing or as a barrier membrane for GBR, the inclusion of a nanofiber layer enables an attainment of biocompatibility, shielding, long-term drug-releasing, and an improvement of rigidity by a reinforcement pattern that mechanically reinforces the nanofiber layer. A nanofiber mat that exhibits high flexibility and elasticity for the ease of handling and is sufficiently structurally reinforced while being not limited to a particular shape can be produced. Also, by having a wide range of usability as a mat including the ease of handling, it can be used in various fields without being limited to conventional and restrictive ways of use.

Particularly, it may be easily used as a mat for cell culturing, by utilizing the reinforcement pattern, which provides well-defined partitions in nanofiber mat, and by using each of the regions partitioned by the reinforcement pattern as a region for cell culturing. When it is used as a mat for cell culturing, it is advantageous in that many types of cells can be cultured at the same time at different regions, because the migration of cells can be restricted by regions by the reinforcement pattern. As a result, the mat can be used in compartmental culturing of various cells/tissues.

Also, the shape of the reinforcement pattern can be controlled variously. Therefore, applying the barrier membrane in various areas of a human body can be facilitated, and the rigidity and flexibility of the barrier membrane can be controlled.

MODES OF THE INVENTION

Hereinafter, exemplary embodiments of the present invention will be described in detail with reference to the accompanying drawings. While the present invention may be subject to various modifications and have variations, only a few particular exemplary embodiments will be described in detail hereinafter. However, there is no intention to limit the present invention to the particular exemplary embodiments, and it should be understood that the scope of the present invention encompasses all modifications, equivalents or alterations made within the spirit and scope of the present invention.

Terms such as "a/the first" and "a/the second" may be used to describe various elements of the present invention, but the elements should not be limited to the terms. Such terms are used to merely distinguish one element from the other(s). For example, "the first element" may also be named "the second element," and similarly, "the second element" may also be named "the first element," without departing from the scope of the present invention.

The terms in the present invention are used to merely describe particular exemplary embodiments and are not intended to limit the present invention. The expression in the singular form covers the expression in the plural form unless otherwise indicated. In describing the present invention, it will be understood that terms such as "contain," "containing," "include," "including," "comprise," "comprising,"

"have" and "having" specify that the features, elements and the like disclosed herein are present, but the terms do not preclude the possibility that one or more other features, elements and the like are also present or may be introduced, within the scope of the present invention.

Unless defined otherwise, all terms, including technical or scientific terms, used herein have the same meaning as commonly understood by a person of ordinary skill in the technical field to which the present invention belongs. Generally used terms such as those defined in a dictionary shall be construed as having the same meaning in the context of the relevant art and, unless explicitly defined otherwise, do not have an idealistic or excessively formalistic meaning.

Figure 1:
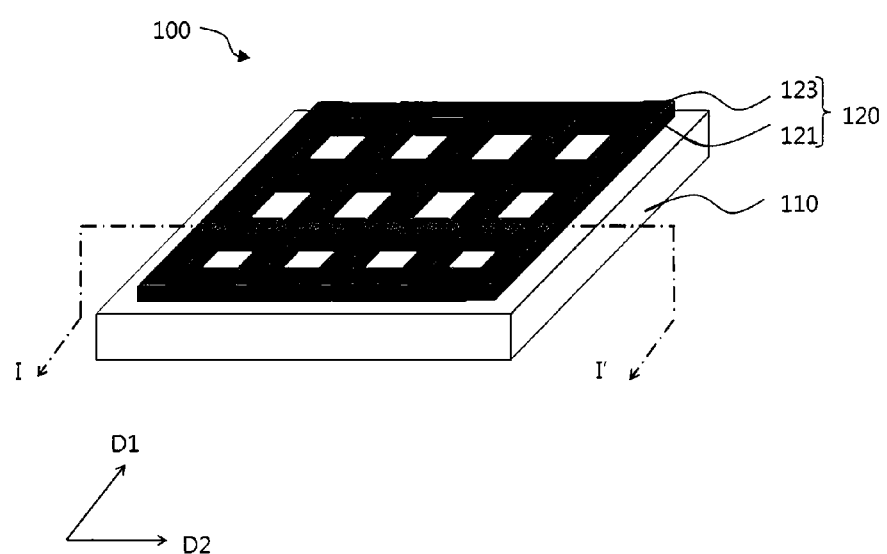
FIG. 1 is a perspective view for describing a nanofiber mat according to one exemplary embodiment of the present invention.

FIG. 1 is a perspective view for describing a nanofiber mat according to one exemplary embodiment of the present invention.

Referring to FIG. 1, a nanofiber mat 100 according to the present invention includes a nanofiber layer 110 and a reinforcement pattern 120. Although not illustrated, the nanofiber layer 110 may be a flat-plate type base substrate, for example, a metal plate or a glass plate. When the flat-plate type base substrate is a glass plate, a metal plate may be disposed below the glass plate.

In one exemplary embodiment, the nanofiber mat 100 according to the present invention may be a nanofiber mat for cell culturing that exhibits biocompatibility that is similar to an environment of a human tissue.

In another exemplary embodiment, the nanofiber mat 100 according to the present invention may be a barrier membrane for guided bone regeneration (GBR).

The nanofiber layer 110 consists of nanofibers, and thus has porosity. Since the nanofiber layer 110 bears a structural similarity to the extracellular matrix of a human tissue, it may provide a three-dimensional culturing effect in a cell culture.

In addition, the nanofiber layer 110 may be a layer that substantially performs a shielding function in a barrier membrane for GBR 100.

A thickness of the nanofiber layer 110 may range from tens of nanometers (nm) to hundreds of micrometers (μm). When the thickness of the nanofiber layer 110 ranges from tens of nanometers to 10 μm (exclusive), the small thickness of the nanofiber layer 110 may enable an easy observation, with a microscope, of cells being cultured. Also, when the thickness of the nanofiber layer 110 is in a range of 10 μm to hundreds of micrometers, it may be able to provide a thicker three-dimensional environment to cells. Such a thickness of the nanofiber mat may be adjusted by controlling a duration of electrospinning during a manufacturing process of the nanofiber layer 110.

In addition, a diameter of the nanofiber that constitutes the nanofiber layer 110 may range from tens of nanometers to a few micrometers. Although not particularly limited, the diameter ranging from 100 nm to 1 μm is preferable. The nanofiber layer 110 may be a nonwoven fabric-type fiber mat in which nanofibers are irregularly arranged, or it may be a mat having a directional nature in which nanofibers are aligned in one direction. Also, the nanofiber layer 110 may be a fabric-type fiber mat that includes nanofibers aligned only in two directions that cross each other. On the other hand, the nanofiber layer 110 may have a laminated structure of 2 or more selected among the nonwoven fabric-type, the directional-type, or the fabric-type fiber mats, and, in this case, the 2 or more fiber mats may be made of mutually different compounds.

The above nanofiber consists of a polymer. In this case, the polymer that constitutes the nanofiber of the nanofiber layer 110 may have thermoplasticity.

For example, the nanofiber may be made of a non-resorbable synthetic polymer. Examples of the non-resorbable synthetic polymer include synthetic polymers such as nylon, polyacrylic acid (PA), polyacrylonitrile, polyamide, polybenzimidazole (PBI), polycarbonate, polyetherimide (PEI), poly(ethyleneoxide), polyethylene terephthalate (PET), polystyrene (PS), polyethylene (PE), poly(styrene-butadiene-styrene) a triblock copolymer, polysulfone, poly-triethylene terephthalate, polyurethane, polyurethane urea, polyvinyl alcohol, polyvinyl carbazole, polyvinyl chloride, polyvinylpyrrolidone, polyvinylidene fluoride (PVDF), poly (vinylidene fluoride-co-hexafluoropropylene) (P(VDF-HFP)). They may be used either exclusively or in combination with 1 or more of the others.

In another example, the nanofiber may be made of a biodegradable polymer. Examples of the biodegradable polymer include an acrylonitrile-butadiene-styrene copolymer (ABS), polylactic acid (PLA), DegraPol (trade name, Ab Medica, Italy), polycaprolactone (PCL), polydioxanone (PDO), polyglutamic acid (PGA), poly(lactide-co-glycolide) (PLGA), poly(L-lactide-co-ε-caprolactone), polyurethane, polyacrylonitrile (PAN), polypropylene (PP). They may be used either exclusively or in combination with 1 or more of the others.

In still another example, the nanofiber may be formed of a natural polymer. Examples of the natural polymer include Bombyx mori silk fibroin, casein, cellulose acetate, chitosan, collagen, fibrinogen, gelatin, and wheat gluten. They may be used either exclusively or in combination with 1 or more of the others.

On the other hand, the polymer that constitutes the nanofiber may be dissolved at least partially by a solvent. The solvent is not limited to a certain range of solvents, as long as it can dissolve the polymer. Examples of the solvent to be used in the production of the nanofiber include chloroform, dichloromethane, 1,2-dichloroethane, 1,1,2-trichloro ethane, water, n-hexane, n-heptane, acetone, methyl alcohol, formic acid, 1,1,1,3,3,3-hexafluoro-2-propanol (HFIP), ethanol, dimethylformamide, dimethylacetamide, trifluoroacetic acid, t-butyl acetate, chlorobenzene, ethyl acetate, methyl ethyl ketone, and tetrahydrofuran, and the polymer may be dissolved by these solvents at least partially.

The nanofiber layer 110 may further contain a biologically reactive substance.

A biologically reactive substance contained in the nanofiber layer 110 may be disposed as a core in an interior of the nanofiber or disposed as a shell on a surface of the nanofiber. On the other hand, the biologically reactive substance may be mixed with the nanofiber to form the nanofiber layer 110 or it may be provided on a surface of the nanofiber layer 110. The drug-releasing function of the nanofiber mat 100 may be attributed to the above biologically reactive substance.

The biologically reactive substance contained in the nanofiber layer 110 may include various growth-inducing agents, a differentiation-inducing agent such as dexamethasone, ascorbic acid, beta-glycerol phosphate, and trans retinoic acid; or a bioactive factor such as heparin or fucoidan, and they may be included either exclusively or in combination with 1 or more of the others.

On the other hand, the nanofiber layer 110 may contain growth-inducing agents, such as basic fibroblast growth factor (BFGF), BMP-2, and HA, in an interior or on a surface.

Alter, the nanofiber layer 110 may promote cell culturing by containing an electric material and/or a magnetic material, and, when a magnetic material is contained, nano tube/rod, metal particles or carbon particles such as graphene, a carbon nanotube, or the like may be contained in addition to the magnetic material.

When the nanofiber layer 110 further contains a biologically reactive substance, drugs and materials to be released or which may affect cells may be mixed with a solution (prepared for the spinning of a nanofiber) beforehand, and the production of the nanofiber may be carried out in a way so that relatively uniformly mixed materials are distributed in an interior of the nanofiber. In some cases, a coaxial double nozzles may be used to produce a nanofiber with a core/shell structure having the drugs and materials in an interior or on a surface.

The reinforcement pattern 120 exposes the nanofiber layer 110 partially and is connected with the nanofiber layer 110. The reinforcement pattern 120 is formed on the nanofiber layer 110, and partially exposes the nanofiber layer 110 so as not to degrade the shielding function of the nanofiber layer 110. Here, "connect" is defined as a state in which two different elements are physically/mechanically combined with each other, without use of a particular adhesive.

The reinforcement pattern 120 includes first patterned areas 121 that extend along a first direction D1 and are arranged spaced apart along a second direction D2, and second patterned areas 123 that extend along the second direction D2 and are arranged spaced apart along the first direction D1. The first direction D1 and the second direction D2 cross each other and, for example, they may be perpendicular to each other. As the first patterned areas 121 and the second patterned areas 123 cross one another on the nanofiber layer 110, the reinforcement pattern 120 may have a lattice shape with openings through which the nanofiber layer 110 is exposed. For example, the reinforcement pattern 120 may have a shape of a square lattice. In this case, in the nanofiber mat 100, substantially the same level of rigidity may be observed along a horizontal axis and a vertical axis.

Figure 2:
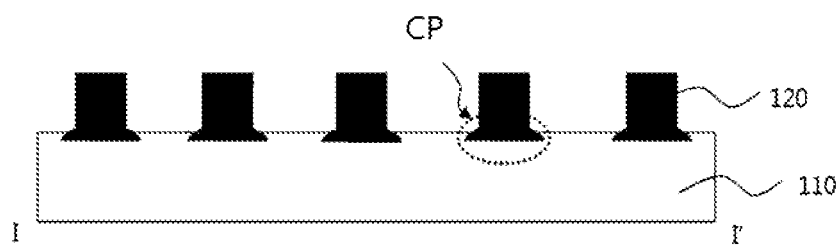
FIG. 2 is a cross-sectional view of FIG. 1 taken along a line I-I'.

FIG. 2 is a cross-sectional view of FIG. 1 taken a line I-I'.

Referring to FIG. 2 along with FIG. 1, as the reinforcement pattern 120 is connected with the nanofiber layer 110, a connection part CP may be formed at an interface thereof, and the coherence between the reinforcement pattern 120 and the nanofiber layer 110 may be improved by the CP. The CP may be formed in a way so that it fills at least a part of an area between a surface and a back surface that faces the surface, of the nanofiber layer 110; that is, the area between the surface and the back surface of the nanofiber layer 110 in a region in which the reinforcement pattern 120 fills partially or fully.

For example, at an interface between the nanofiber layer 110 and the reinforcement pattern 120, the reinforcement pattern 120 may be subjected to melting-solidification together with a part of nanofibers of the nanofiber layer 110 to be combined with the nanofiber layer 110. In this case, the area that underwent melting-solidification may be the CP. During a process of forming the reinforcement pattern 120, when a melt in which materials to constitute the reinforcement pattern 120 are melted is provided to the nanofiber layer 110, as the nanofiber layer 110 melts locally so that it melts (or partially melts) and solidifies together with the materials for constituting the reinforcement pattern 120, the CP is formed and, due to the CP, the coherence between the nanofiber layer 110 and the reinforcement pattern 120 becomes larger. The above melt includes both completely melt or partially melt states of the materials for constituting the reinforcement pattern 120.

On the other hand, when a melt of materials that constitute the reinforcement pattern 120 is provided to the nanofiber layer 110, the reinforcement pattern 120 may partially or fully penetrate into the nanofiber layer 110 and solidify, thus combining with the nanofiber layer 110. Or, when a solution that forms the reinforcement pattern 120 is provided to the nanofiber layer 110, the polymer that makes up the reinforcement pattern 120 may penetrate into the nanofiber layer 110 and solidify, thus combining with the nanofiber layer 110. In this case, a state in which the reinforcement pattern 120 is surrounding nanofibers of the nanofiber layer 110, that is, a state in which the reinforcement pattern 120 are partially filling pores of the nanofiber layer 110 is observed in the CP; therefore, the coherence between the nanofiber layer 110 and the reinforcement pattern 120 may be strengthened due to the CP.

On the other hand, the reinforcement pattern 120 may be combined with the nanofiber layer 110 by dissolving a part of nanofibers constituting the nanofiber layer 110 and then solidifying them together. In this case, in the CP, the reinforcement pattern 120 and the nanofiber layer 110 are combined while being entangled, and thus the coherence between the nanofiber layer 110 and the reinforcement pattern 120 may be strengthened due to the CP.

The materials that make up the reinforcement pattern 120 may be a polymer resin. In this case, the polymer resin may be a synthetic polymer, a biodegradable polymer, or a natural polymer. In this case, the synthetic polymer, the biodegradable polymer, or the natural polymer may be prepared as the above-described materials which are used to form nanofibers of the nanofiber layer 110. Examples of the polymer resin that makes up the reinforcement pattern 120 include ABS, PLA, PDO, PCL, PLGA, PGA, polyurethane, PS, PE, PP, nylon, silk, collagen, gelatin, and agarose.

In the meantime, the polymer resin constituting the reinforcement pattern 120 can be used along with a solvent in a state of a solution for the preparation of the reinforcement pattern 120, and a solvent in which the nanofiber layer 110 is insoluble or poorly soluble may be used as the solvent. The solvent that makes up a solution for the formation of the reinforcement pattern 120 constitutes a solution along with a polymer resin which is selected for the reinforcement pattern, and it is preferable that a solvent in which nanofibers of the nanofiber layer 110 are insoluble or poorly soluble is used so as not to affect nanofibers of the nanofiber layer. In other words, it is preferable that the materials constituting the reinforcement pattern 120 made into a liquid(s) is used as the solvent making up the solution that forms the reinforcement pattern 120, and that the selected solvent does not dissolve nanofibers of the nanofiber layer 110. Examples of the solvent making up the solution that forms the reinforcement pattern 120 include water, chloroform, dichloromethane, 1,2-dichloroethane, 1,1,2-trichloroethane, water, n-hexane, n-heptane, acetone, methyl alcohol, formic acid, 1,1,1,3,3,3-hexafluoro-2-propanol (HFIP), ethanol, dimethylformamide, dimethylacetamide, trifluoroacetic acid, t-butyl acetate, chlorobenzene, ethyl acetate, methyl ethyl ketone, and tetrahydrofuran. However, considering the polymer properties of the nanofiber, a solvent with low reactivity is required.

The polymer that constitutes the reinforcement pattern 120 may be substantially the same as the material that makes up the nanofiber layer 110. When the reinforcement pattern 120 and the nanofiber layer 110 are made of the same material, the reinforcement pattern 120 and the nanofiber layer 110 may undergo melting-solidification and become physically firmly connected (combined). On the other hand, the reinforcement pattern 120 and the nanofiber layer 110 may be made of mutually different types of polymers.

In the meantime, the reinforcement pattern 120 may further contain a biologically reactive substance. The biologically reactive substance that is included in the reinforcement pattern 120 is a compound that can induce or improve osseous tissue regeneration, and hydroxyl apatite may be an example.

As the reinforcement pattern 120 is formed in the nanofiber mat 100, the nanofiber layer 110, in a region on which the reinforcement pattern 120 is formed, forms the CP with a significantly higher density in comparison to the original density by the arrangement of nanofibers.

The CP may be formed deeper than what is illustrated in FIG. 2, and it may even fully fill between a surface and a back surface of the nanofiber layer 110 in a region in which the reinforcement pattern 120 is formed. By this, when a plurality of regions, partitioned by the reinforcement pattern 120, in the nanofiber mat 100 are provided with different types of cells for cell culturing, the migration of cells being cultured to other regions may be blocked. In other words, in the nanofiber layer 110, starting from a first plane of the nanofiber layer 110 where the reinforcement pattern 120 is formed outward, the reinforcement pattern 120 may not only protrude but may also fill between the first plane and the second plane, which is a plane on an opposite side of the first plane, and such a structure may enable a blockage of the migration of materials (e.g. cells being cultured) to other regions. Like this, the nanofiber mat 100 that was described in FIG. 1 and FIG. 2 bears a similarity to an environment of a human tissue and can restrict a migration of cells being cultured, while minimizing a change in an appearance, and thus it is suitable as a nanofiber mat that is capable of culturing different cells by section. Particularly, the arrangement of nanofibers constituting the nanofiber layer 110 may be variously controlled, but when a nanofiber mat for cell culturing employs a nanofiber layer 110 that is aligned in one direction, it becomes easier to observe the growth and migration of cells in one direction.

Also, the CP may be made thinner than what is illustrated in FIG. 2. When a depth measured from a surface of the nanofiber layer 110 of the CP is shallower than what is illustrated in FIG. 2 or the same as what is illustrated in FIG. 2 and distinct types of cells are provided in each region of the nanofiber mat 100, which was partitioned into a large number of regions by the reinforcement pattern 120, it is possible for the cells being cultured to migrate through the nanofiber layer under a reinforcement. Accordingly, it may be possible to observe a behavior of cells and culture tissues consisting of multiple cells in an environment consisting of various cells.

Not only that, when various cell suspensions are sprayed by section using a pipette, cell culturing with a complex shape may be possible by the CP.

Further, when a nanofiber mat consisting only of the nanofiber layer 110 and not including the reinforcement pattern 120 absorbs moisture or becomes wet during a procedure using a barrier membrane, two planes, with a folded part in the middle, stick together and it is very difficult to unfold them into a flat sheet again.

Also, when a barrier membrane not including a reinforcement pattern 120 absorbs moisture, several sheets stick together and become very difficult to handle. However, like in a case of the nanofiber mat 100 according to the present invention, the formation of the reinforcement pattern 120 results in elasticity and restitution by the reinforcement pattern 120, thus enabling easy handling, while having a certain level of flexibility that is inherent in a nanofiber layer. Also by making changes to a shape of the reinforcement pattern 120, a barrier membrane suitable for a complex structure of an area of a human body that requires a procedure can be provided.

Figure 3:
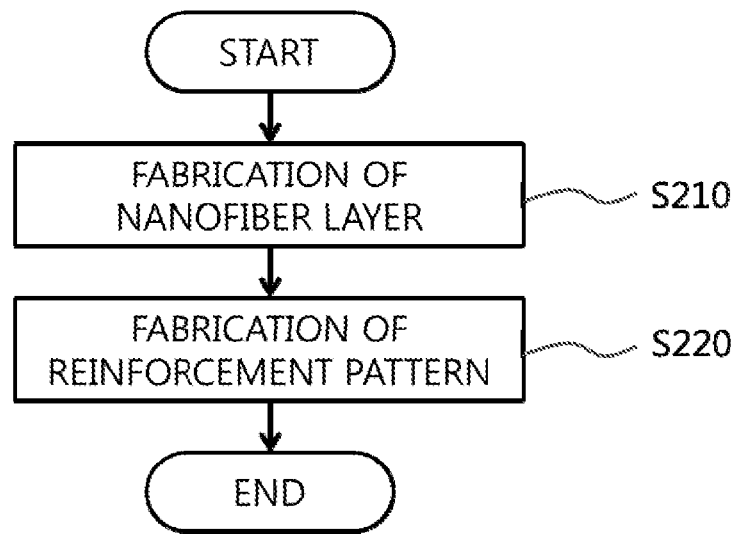
FIG. 3 is a flowchart for describing a method of manufacturing a nanofiber mat according to one exemplary embodiment of the present invention.
Figure 4:
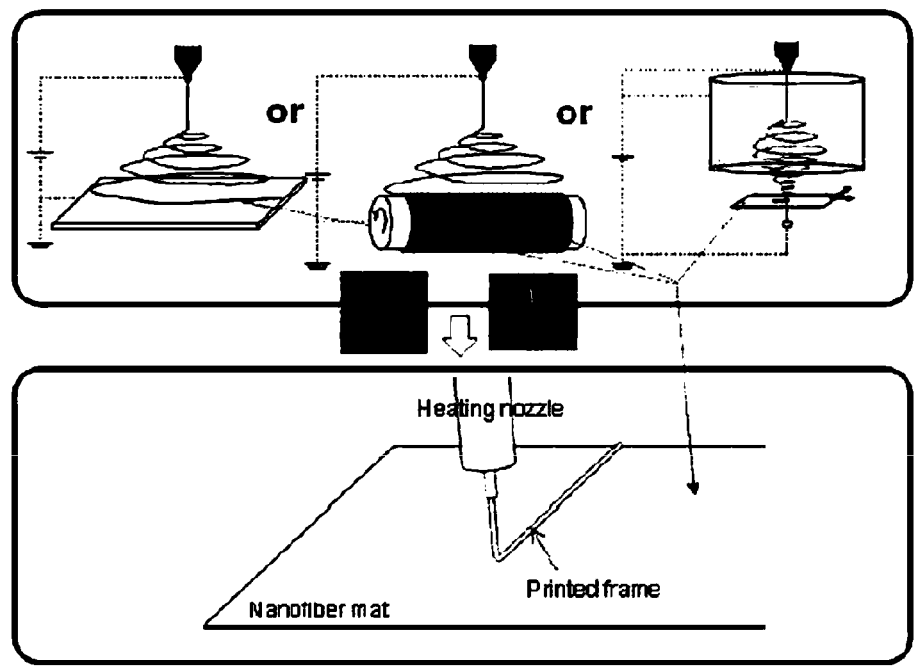
FIG. 4 illustrates a method of manufacturing the nanofiber mat of FIG. 3.
Figure 5:
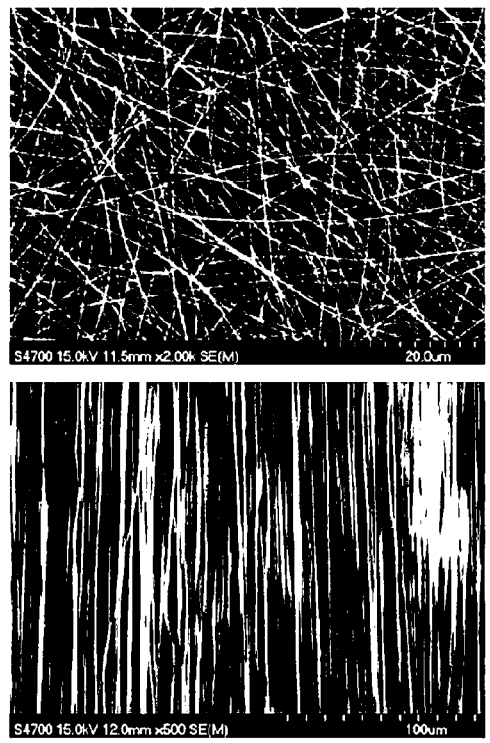
FIG. 5 is an electron microscopic image of a nanofiber layer. (First figure: randomly deposited nanofibers; Second aligned nanofibers)

FIG. 3 is a flowchart for describing a method of manufacturing a nanofiber mat according to one exemplary embodiment of the present invention, FIG. 4 illustrates a method of manufacturing the nanofiber mat of FIG. 3, and FIG. 5 is an electron microscopic image of a nanofiber layer.

In FIG. 4, an upper image illustrates electrospinning by which the nanofiber layer 110 is formed, and a lower image describes a process of forming the reinforcement pattern 120.

Referring to FIG. 3, FIG. 4, and FIG. 5, in a process of manufacturing a nanofiber mat 100, first, a nanofiber layer 110 is formed (S210).

The nanofiber layer 110 may be formed by a general method of electrospinning for fibers. During the process of forming the nanofiber layer 110, biologically reactive substances may be additionally included in materials constituting nanofibers. A produced nanofiber layer 110, as shown in an upper photographic image of FIG. 5, may have a structure in which nanofibers are randomly arranged or, as seen in a lower photographic image of FIG. 5, a structure in which nanofibers are aligned in one direction.

For example, the nanofiber layer 110 may be a nonwoven fabric-type fiber mat.

For example, the nanofiber layer 110 may be fabricated by electrospinning on a flat metal plate as seen in a diagram on the left hand side of the upper image of FIG. 4 and spinning nanofibers on the metal plate. In this case, a glass plate may be further installed on top of the metal plate.

On the other hand, as seen in a diagram in the middle of the upper image of FIG. 4, the nanofiber layer 110 may be produced by electrospinning using a drum collection screen (collector) into a fiber mat with a directional nature, which is aligned in one direction, and, as seen in a diagram on the right hand side of the upper image of FIG. 4, a nanofiber layer having a particular pattern, or a uniform or a specifically controlled thickness or density distribution may be produced by direct-write electro spinning (DWES) or the like. The process of electrospinning may be carried out using a voltage in a range of about 5 to 30 kV so that nanofibers can be collected on a glass collector with a thickness in a range of about 100 to 200 μm. In this case, a distance between the glass plate and a nozzle may range from 3 to 10 cm, a diameter of the nozzle may range from 100 to 500 μm. Also, the flow rate in this case may range from 0.05 to 0.5 ml/h. A diameter of a cylinder-type side electrode may be in a range of 10 to 20 cm.

When electrospinning using a drum collector is used, the nanofiber layer 110 consisting of nanofibers that are aligned in one direction may be prepared by rolling a metal thin film (e.g. aluminum foil) or a polymer thin film (e.g. wrap or polymer film) on the drum collector, spinning nanofibers on the thin film, and then unrolling the thin film on which the nanofibers were spun. Additionally, the nanofiber layer 110 including a fiber mat that is aligned in different directions may be prepared by two electrospinning processes.

In this case, for a general electrospinning process and an electrospinning process using a drum as a collector, a few to tens of kilovolts (kV) of voltages may be applied and a collector-to-nozzle distance may be in a range of a few to hundreds of millimeters. An inner diameter of the nozzle may range from tens of micrometers to a few millimeters. A flow rate may be in a range of 0.01 to 10 ml/h, and a plurality of nozzles may be used at the same time. The rotational speed of the drum may range from a few to thousands of rpm, and when the speed ranges from a few to hundreds of rpm, the nanofibers may be collected randomly on the drum; in contrast, when the speed is in a range of hundreds to thousands of rpm, the alignment tends to be improved. In this case, a radius of the drum affects the result as well; an exact relationship is that the alignment is achieved when a linear speed on a surface of the drum is equal to or greater than a speed of nanofiber generation, and when the linear speed is significantly lower than the speed of fiber generation, the fibers are randomly collected.

Subsequently, a nanofiber layer 110 is formed, and then a reinforcement pattern 120 is formed thereon (S220).

The reinforcement pattern 120 may be formed by printing a first patterned area 121 and a second patterned area 123. A pattern forming device 300 (see FIG. 4) that forms the reinforcement pattern 120 is a device that prints a polymer resin, and it may be a three-dimensional (3D) printing device. It may be a device that prints a polymer resin in a state of a melt or a solution. An exemplary 3D printing device may be a fused deposition modeling (FDM) device.

In an example of a polycaprolactone (PCL) material, a melting temperature may be in a range of about 80 to 120° C., and a pressure may be in a range of 300 to 1,000 kPa. In this case, a scanning speed may be from a few millimeters per minute to thousands of millimeters per minute, for example 100 mm/minute. A diameter of a nozzle used in an FDM process may be from 100 μm to a few millimeters, and a distance from the nozzle to the nanofiber layer may be in a range of 50 μm to 1 mm.

Figure 6:
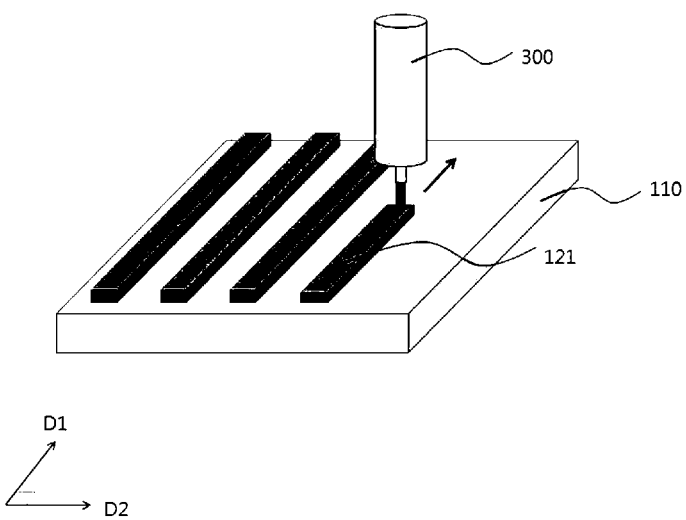
FIG. 6 and FIG. 7 illustrate a process of fabrication a reinforcement pattern.
Figure 7:
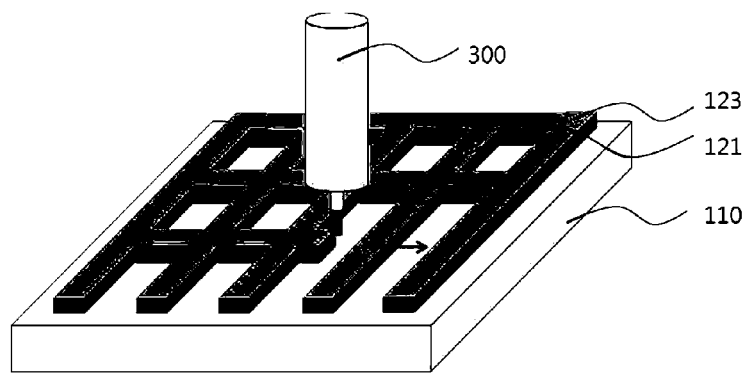
Figure 7:
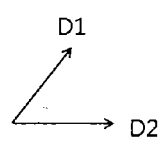

FIG. 6 and FIG. 7 illustrate a process of forming a reinforcement pattern.

Referring to FIG. 6, the first patterned area 121 may be prepared by moving the pattern forming device 300 in the first direction D1 on the nanofiber layer 110. The pattern forming device 300 heats a polymer resin (e.g. a thermoplastic resin) to provide it to the nanofiber layer 110 in a molten state. In this case, biologically reactive substances may be added, together with the polymer resin, to the pattern forming device 300.

For example, a first bar pattern is produced by providing a melt while moving the pattern forming device 300 from one region at an edge of the nanofiber layer 110 in the first direction D1, and a second bar pattern is formed by providing the melt while moving the pattern forming device 300, from the first bar pattern, to a certain distance in the second direction D2 and then again in the first direction D1. By repeating the above-described processes, the first patterned area 121 may be formed.

As the pattern forming device 300 provides a high-temperature melt to the nanofiber layer 110, a part of the nanofiber layer 110 may be also melt due to a temperature of the melt. As the melt and nanofibers of the nanofiber layer 110 cool and solidify, the first patterned area 121 and the nanofiber layer 110 are firmly connected to each other. Or, the melt may penetrate into the nanofiber layer 110, which was not melted, and solidify. Since the nanofiber layer 110 has porosity, molten thermoplastic resins may combine with the nanofiber layer 110 by filling some parts of voids thereof. Like this, the CP that is formed by melting-solidification or penetration-solidification may improve the coherence between the first patterned area 121 and the nanofiber layer 110.

Referring to FIG. 7, the second patterned area 123 may be produced by moving the pattern forming device 300 in the second direction D2 on the nanofiber layer 110, on which the first patterned area 121 has been formed. Since a process of forming a bar pattern of the second patterned area 123 is substantially the same as the process of forming the bar pattern of the first patterned area except for a direction in which the pattern forming device 300 moves, repetitive and detailed descriptions thereof will be omitted.

In a process of forming the second patterned area 123, as nanofibers of the nanofiber layer 110 are partially melted by the melt and then solidify, the CP may be formed, and the coherence between the second patterned area 123 and the nanofiber layer 110 may be enhanced. At the same time, in the process of forming the second patterned area 123, the region in which it intersects the first patterned area 121 is again subjected to melting-solidification, and thus the coherence between the first patterned area 121 and the second patterned area 123 may also be improved.

Accordingly, the nanofiber mat 100 illustrated in FIG. 1 and FIG. 2 is produced.

In the meantime, when the reinforcement pattern 120 is formed by printing and using a solution containing a polymer resin, which is a material for the reinforcement pattern 120, and a solvent, the solvent may dissolve some parts of nanofibers of the nanofiber layer 110. As the solution partially dissolves the nanofibers and solidifies, the coherence between the reinforcement pattern 120 and the nanofiber layer 110 may be improved. In this case, it is preferable that the solution dissolves nanofibers in a region to which the solution is directly sprayed, while not affecting other regions.

As described in FIGS. 3 to 7, by printing a solution or a melt on the nanofiber layer 110 using the pattern forming device 300, the reinforcement pattern 120 may be easily formed, and the coherence between the reinforcement pattern 120 and the nanofiber layer 110 may be maximized. Accordingly, the nanofiber mat 100 may be suitably used for cell culturing or as a GBR barrier membrane.

Figure 8:
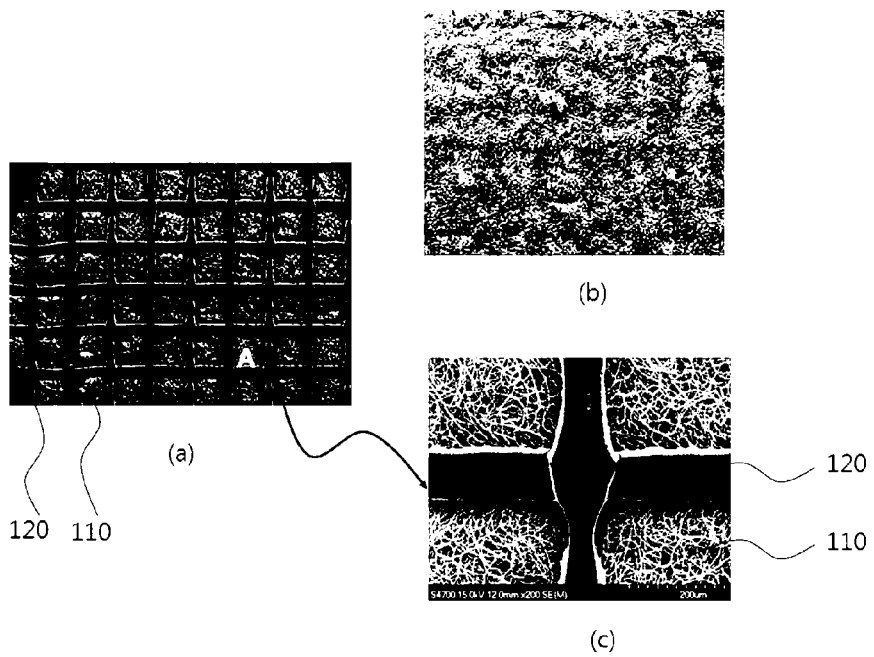
FIG. 8 is a view representing scanning electron microscopic (SEM) images of a nanofiber mat according to one exemplary embodiment of the present invention.

FIG. 8 is a view representing scanning electron microscopic (SEM) images of a nanofiber mat according to one exemplary embodiment of the present invention.

In FIG. 8, (a) is a SEM image showing a top view of a nanofiber mat whose structure is substantially the same as that of the nanofiber mat 100 shown in FIG. 1, (b) is a SEM image showing a rear view of (a), and (c) is an enlarged SEM image showing a top view of a region A of (a). The images in FIG. 8 are photographed images of a nanofiber mat produced by the process described in FIGS. 3 to 7 that were taken by an scanning electron microscope.

The nanofiber layer of the nanofiber mat illustrated in FIG. 8 was formed by electrospinning on a glass collector with a thickness of about 150 μm using a solution in which PCL was mixed with chloroform (a solvent) at a concentration of about 8.8 wt % and a voltage of about 15 kV. In this case, a distance between the glass collector and a nozzle was 70 mm and an inner diameter of the nozzle was about 150 μm, and a flow rate was 0.1 ml/h. A diameter of a cylinder-type side electrode was about 160 mm.

Subsequently, a reinforcement pattern having of the filaments with a diameter of 100 μm and height of 80 μm was formed by an FDM process using the nanofiber layer, produced as above, and the solution. In this case, a melting temperature was about 100° C. and a pressure was 600 kPa, and a scanning speed was 100 mm/min. A diameter of a nozzle used in the FDM process was about 150 μm and a distance between the nozzle and the nanofiber layer was 150

µm. Referring to FIG. 8 along with FIG. 1, the first patterned area 121 and the second patterned area 123 were formed with a uniform diameter on the nanofiber layer 110, which includes a nonwoven fabric-type fiber mat, and were obtained by electrospinning.

As seen in FIG. 8(b), the back surface of the nanofiber layer 110 maintains an original surface of the nanofiber layer 110, and in (c), the reinforcement pattern 120 is physically combined with the nanofiber layer 110. Specifically, an edge of the reinforcement pattern 120 is attached to the nanofiber layer 110 by melting, and thus the reinforcement pattern 120 and the nanofiber layer 110 are actually connected to each other by the CP that was described in FIG. 2.

Figure 9:
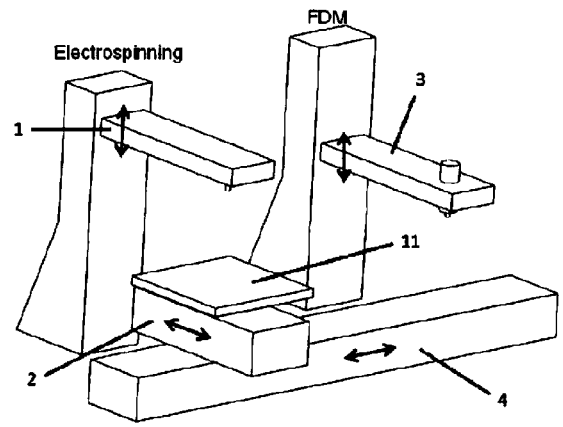
FIG. 9 illustrates a nanofiber-mat manufacturing device that forms a nanofiber layer and a reinforcement pattern.

FIG. 9 illustrates a nanofiber-mat manufacturing device that forms a nanofiber layer and a reinforcement pattern.

In FIGS. 4 to 7, electrospinning equipment and an independent pattern forming device 300 were illustrated, and descriptions were provided with reference to the drawings, but the pattern forming device 300 may be combined with the electrospinning equipment, as illustrated in FIG. 9, to constitute a barrier membrane forming device that forms the barrier membrane 100 illustrated in FIG. 1 and FIG. 2. In this case, an electrospinning process and a printing process may be sequentially carried out by the barrier membrane forming device to produce a barrier membrane 100.

Referring to FIG. 9, specifically, in a single production device, nanofibers are collected by electrospinning equipment and the collector moves, so that the reinforcement pattern 120 is printed on the nanofiber layer 110 by an FDM device. Four basic stages (1, 2, 3, 4) are used, a slab 11 is installed on a stage 2 that moves on an X-Y plane. Here, an electrode such as a plate, a block, or a line is attached to the slab, which may be used as a collector after a metal thin film or an insulating sheet is attached thereon.

Figure 10:
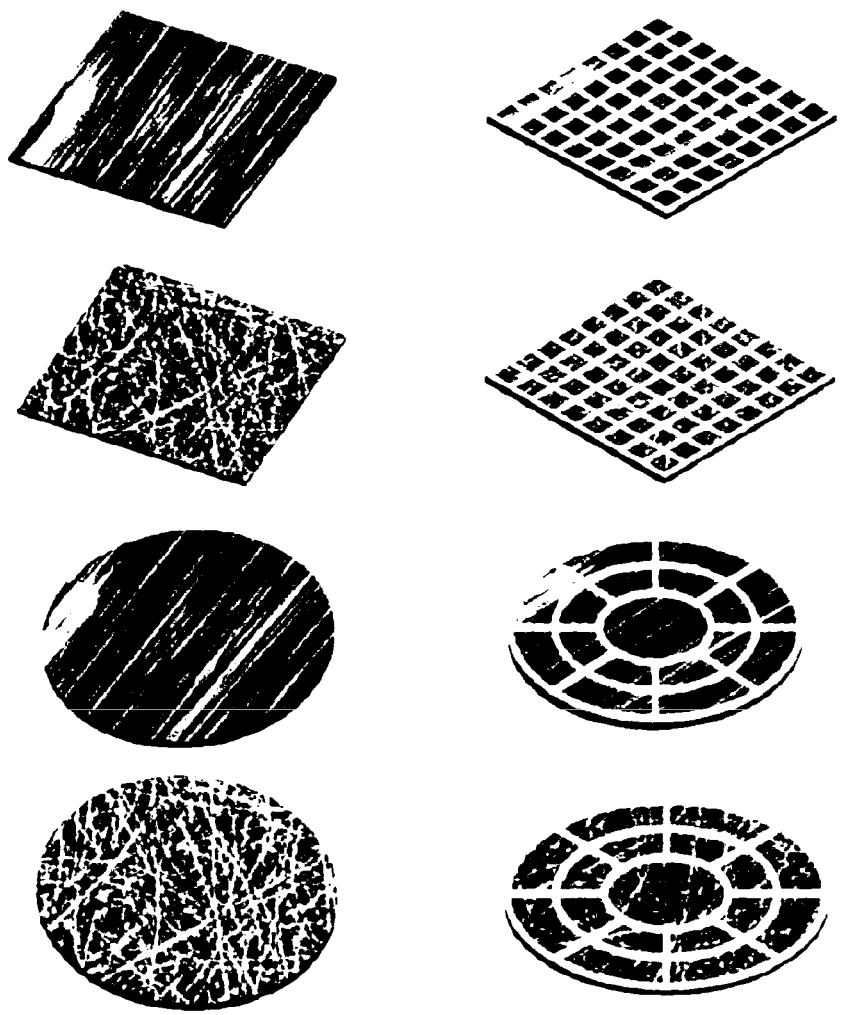
FIG. 10, FIG. 11, and FIG. 12 illustrate a planar structure of nanofiber mats, provided in various structures, of the present invention.
Figure 11:
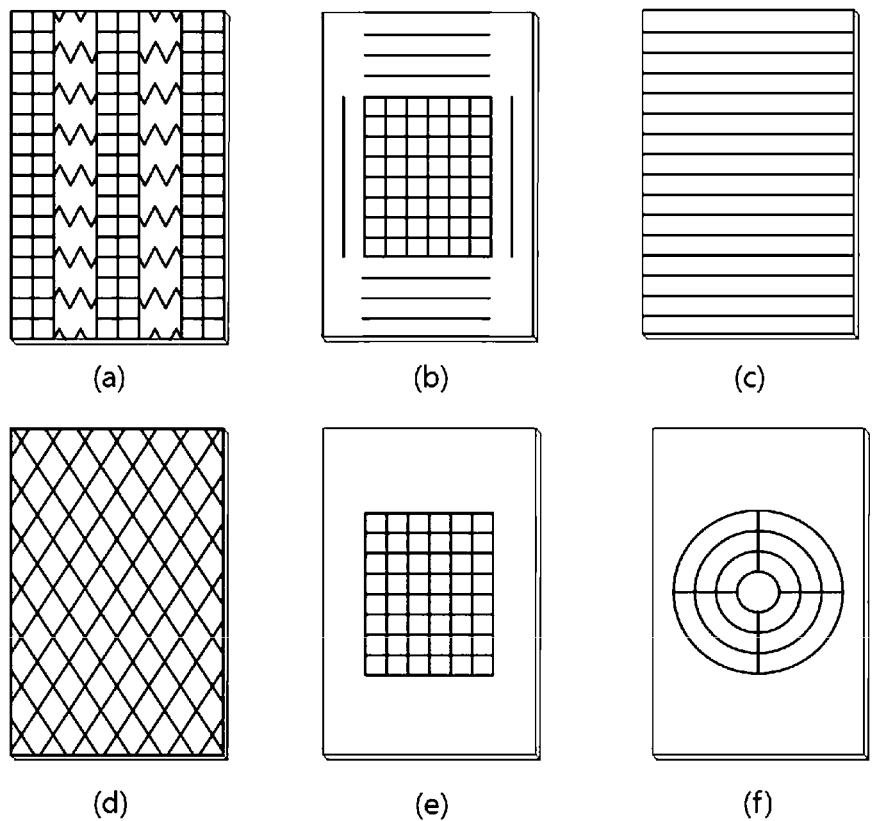
Figure 12:
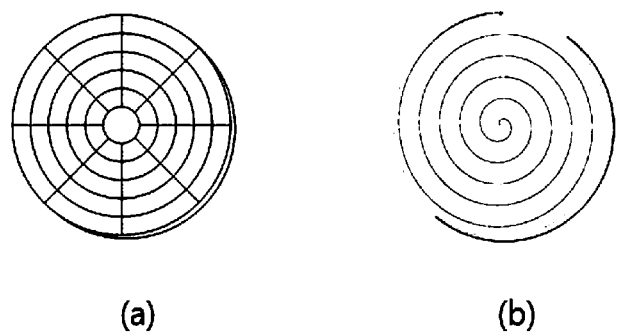

FIG. 10, FIG. 11, and FIG. 12 illustrate a planar structure of nanofiber mats, provided in various structures, of the present invention.

The nanofiber mat of FIG. 10 has a structure that is suitable both for cell culturing and as a barrier membrane, and the nanofiber mats of FIG. 11 and FIG. 12 have a structure that is particularly appropriate as a barrier membrane.

In FIG. 10, images on the right correspond to planes with a reinforcement pattern 120, and images on the left shows a rear side of nanofiber layers 110 without a reinforcement pattern 120. Referring to the images, a lattice-type reinforcement pattern or a reinforcement pattern having a concentric circle structure may be constructed. A nanofiber layer 110 may have nanofibers arranged in one direction and a lattice-type reinforcement pattern; on the other hand, the nanofiber layer 110 may have nanofibers that are randomly arranged and a lattice-type reinforcement pattern on the nanofibers. Also, when the nanofiber layer 110 is circular, it may have a reinforcement pattern having a concentric circle structure and including reinforcements in a radial direction, and a level of reinforcement of rigidity may be controlled by satisfying the spacing, thickness, and number of levels of the reinforcement pattern or by installing connecting rods that connects the reinforcement pattern having a concentric circle structure.

In the meantime, referring to FIG. 11, a reinforcement pattern shown in (a) includes a zigzag-type subpattern in addition to a square lattice-type subpattern. The reinforcement pattern that is shown in (a) has a certain level of rigidity due to the square lattice-type subpattern, and also has relatively lower rigidity in comparison to the square lattice-type subpattern, which is flexibility, due to the zigzag-type subpattern. In other words, when bending occurs in a horizontal direction (width direction) of (a), the pattern bends easily in the horizontal direction because it has rigidity due to a square lattice-type subpattern, but the zigzag-type subpattern mainly bends. In this case, the zigzag-type subpattern offers the nanofiber layer a certain level of rigidity, which is lower than the rigidity of the square lattice-type subpattern.

The reinforcement pattern shown in (b) is a structure in which a square lattice-type subpattern is disposed in a central area so that high rigidity can be attained, and a linear subpattern is additionally combined in a peripheral area so that rigidity exists only in a horizontal direction and a vertical direction. In the case of a linear subpattern in the horizontal direction, it reinforces rigidity only in the horizontal direction. Also, in a region without a reinforcement pattern, the nanofiber layer exhibits flexibility. That is, the structure may be used as a structure in which the central area is maintained flat and the peripheral area droops in a direction of the force of gravity.

The reinforcement pattern shown in (c) includes a linear reinforcement pattern in a horizontal direction, and thus reinforces rigidity only in one direction of the barrier membrane. Although not shown in a drawing, the barrier membrane may also include a linear reinforcement pattern in a vertical direction.

The reinforcement pattern of (d) has a structure of a rhombic lattice-type reinforcement pattern, and, as a result, rigidity in a diagonal direction is higher than rigidity in an X-Y direction of a plane. In the reinforcement pattern of (e), a square lattice-type reinforcement pattern is formed only in a central area of the barrier membrane so that the rigidity of the structure can be reinforced only locally. In a structure of a barrier membrane of (e), the central area exhibits rigidity due to the reinforcement pattern, but the peripheral area, which is a region without the reinforcement pattern, still maintains the flexibility of the nanofiber layer.

Also, the reinforcement pattern shown in (f) has a structure in which a circular lattice shape is formed only in a central area of the barrier membrane to enhance rigidity. When a circular lattice-type reinforcement pattern is prepared on a nanofiber layer with a flat rectangular shape as in (f), it may be usefully employed for alveolar bone regeneration during an implant procedure. In a barrier membrane structure as shown in (f), the central area exhibits rigidity, and the peripheral area (the region without a reinforcement pattern) has the original flexibility of a nanofiber layer. Also, a hole that penetrates the central area of the nanofiber layer, where the reinforcement pattern shown in (f) is developed, may be formed and used as a bolting hole for an implant.

According to the above description, the rigidity of a resorbable polymer nanofiber mat 100 may be improved by the reinforcement pattern 120 that mechanically reinforces the nanofiber layer 110, while shielding, biocompatibility, long-term drug-releasing, and the like, which are inherent in the nanofiber mat 100, are still maintained by the nanofiber layer 110.

As seen in FIG. 11, since a shape of the reinforcement pattern 120 may be variously controlled by the pattern forming device 300, the nanofiber mat 100 may be easily applied to various areas of a human body, and the rigidity and flexibility of the nanofiber mat 100 may be controlled.

FIG. 12 shows a structure of a reinforcement pattern formed on a nanofiber layer that has a flat circular shape structure. The reinforcement pattern shown in (a) may improve the rigidity of the nanofiber mat in radial and circumferential directions. In this case, a hole that penetrates the central area of the circular nanofiber layer, where the reinforcement pattern shown in (a) is developed, may be formed and used as a bolting hole for an implant.

The reinforcement pattern shown in (b) has a curved shape structure and may have a spiral shape. The reinforcement pattern shown in (b) has relatively lower rigidity and higher flexibility, when rotated, as compared with (a). Specifically, the curved shape structure shown in (b) attains flexibility when rotated, and thus when a torque is applied along a longitudinal direction of the curved shape, which is also a longitudinal direction of the reinforcement pattern, while fixing the central area, the nanofiber layer contracts while being distorted, causing a diameter of the barrier membrane to decrease. That is, as the barrier membrane is distorted, the nanofiber layer that corresponds to the region without a reinforcement pattern becomes folded, and spacing between reinforcement patterns, which are facing each other, becomes narrower. In this case, when inserted into an area having a shape of a hole that requires a medical procedure and then the torque is removed, the barrier membrane may become relaxed inside the hole due to the reinforcement pattern, resulting in the partial restoration and stable disposition of the barrier membrane. As described, the barrier membrane with a reinforcement pattern (shown in (b)) may be used for pre-tensioning during a time of a procedure.

A barrier membrane having a reinforcement pattern of FIG. 12(*a*) and (*b*) may be easily used for the regeneration of a skull during a time of skull drilling. The structure of the reinforcement patterns described with reference to FIGS. 10 to 12 are mere examples and are intended not to limit the present invention thereto. In the above description, reinforcement patterns with a single structure were shown and described, but the patterns may be constructed to have 2 or more layers, and 2 or more of reinforcement patterns with various structures may be used in combination.

EXAMPLE 1

A 9 wt % solution prepared by dissolving PCL with a number average molecular weight (Mn) of about 80,000 in chloroform was electrospun to a 150-μm thick glass collector under process conditions including a spinning distance (nozzle-to-collector distance) of 70 mm, voltage of 20 kV, and a flow rate of 0.1 ml/h. On the produced nanofibers, a reinforcement pattern was printed by an FDM process and using a PCL-melt under process conditions including a temperature of 100° C., pressure of 600 kPa, scanning speed of 100 mm/min, nozzle diameter of 150 μm, and a jetting distance of 150 μm. A thickness of the obtained nanofiber mat was 100 μm, and a diameter of the reinforcement was 150 μm.

EXAMPLE 2

A 9 wt % solution prepared by dissolving PCL with a Mn of about 80,000 in chloroform was electrospun to a drum-shaped collection screen, which rotates at 3000 rpm, under process conditions including a spinning distance of 70 mm, voltage of 20 kV, and a flow rate of 0.1 ml/h. After spinning, the cylindrical nanofiber was cut flat. On the produced nanofibers, a reinforcement pattern was printed by an FDM process and using a PCL-melt under process conditions including a temperature of 100° C., pressure of 600 kPa, scanning speed of 100 mm/min, nozzle diameter of 150 μm, and a jetting distance of 150 μm. A thickness of the obtained nanofiber mat was 120 μm, and a diameter of the reinforcement was 150 μm.

EXAMPLE 3

A 9 wt % solution was prepared by dissolving 500 mg of PCL with a Mn of about 80,000 in chloroform. 10 μg of BMP-2 and 50 mg of PEG were dissolved in 2 ml of DCM, added to the PCL solution previously prepared, and stirred thoroughly for 30 minutes. Then, it was electrospun to a 150-μm thick glass collector under process conditions including a spinning distance of 70 mm, voltage of 20 kV, and a flow rate of 0.1 ml/h. On the produced nanofibers, a reinforcement pattern was printed by an FDM process and using a PCL-melt under process conditions including a temperature of 100° C., pressure of 600 kPa, scanning speed of 100 mm/min, nozzle diameter of 150 μm, and a jetting distance of 150 μm. A thickness of the obtained nanofiber mat was 100 μm, and a diameter of the reinforcement was 150 μm.

Disclosed descriptions of exemplary embodiments are provided to allow those with ordinary skill in the technical field of the present invention to use or implement the present invention. Various modifications of such exemplary embodiments will be apparent to those with ordinary skill in the art, and the generic principles defined herein may be applied to other exemplary embodiments without departing from the scope of the present invention. Hence, it should be understood that the present invention is not intended to be limited to the embodiments shown herein, and that it should be interpreted in the broadest scope that is consistent with the principles and novel features disclosed herein.

The invention claimed is:
1. A nanofiber mat, comprising:
a nanofiber layer; and
a reinforcement pattern that is disposed on the nanofiber layer,
wherein the nanofiber layer and the reinforcement pattern are combined with each other through an interface formed by melting-solidification of at least a part of the nanofiber layer together with the reinforcement pattern such that the interface comprises at least a portion of melted nanofiber layer and at least a portion of melted reinforcement pattern;
wherein the reinforcement pattern fills between a surface, on which the reinforcement pattern is formed, and a back surface of the nanofiber layer at least partially so that a migration of a material is restricted by the reinforcement pattern,
wherein the nanofiber mat has a planar shape and the thickness of the nanofiber layer ranges from 10 nm to 10 μm;
wherein the reinforcement pattern includes at least two subpatterns having mutually different shapes, and rigidity of regions in which the subpatterns are formed are mutually different; and
wherein the subpatterns have a shape of at least one selected among a square lattice, a circular lattice, a rhombic lattice, a zigzag, and a curve.

2. The nanofiber mat of claim 1, wherein any one of the nanofiber layer and the reinforcement pattern includes at least one of biologically reactive substances, magnetic materials, and electric materials.

3. The nanofiber mat of claim 1, wherein the nanofiber layer includes a structure in which nanofibers are randomly arranged, aligned along one direction, or arranged in two directions, where one direction intersects the other.

4. The nanofiber mat of claim 1, wherein the reinforcement pattern is formed in a central area of the nanofiber layer and improves rigidity of the central area, and a peripheral area of the nanofiber layer, which surrounds the central area, is a region where the reinforcement pattern is not formed and has flexibility due to the nanofiber layer.

5. The nanofiber mat of claim 1, wherein the reinforcement pattern has a curved shape with a spiral structure, and when a torque is applied along an axial direction of the spiral structure, the nanofiber layer contracts, and when the torque is removed, the contracted nanofiber layer is relaxed and at least partially restored.

6. The nanofiber mat of claim 1, wherein the nanofiber mat is a nanofiber mat for cell culturing.

7. The nanofiber mat of claim 1, wherein the nanofiber mat is a barrier membrane for guided bone regeneration (GBR).

8. A method of manufacturing a nanofiber mat of claim 1, the method comprising: preparing a nanofiber layer; and forming a reinforcement pattern by, printing, on the nanofiber layer, a polymer resin in a state of a polymer melt or a polymer solution.

9. The method of claim 8, wherein, during the forming of a reinforcement pattern, at least a part of the nanofiber layer is melted by the polymer melt or polymer solution, and the nanofiber layer at least partially melted solidifies together with the polymer melt or polymer solution to form the reinforcement pattern.

10. The method of claim 8, wherein the forming of a reinforcement pattern, a fused deposition modeling (FDM) device is used.

11. The method of claim 8, where the solution or the melt penetrates into the nanofiber layer and solidify together with the nanofiber layer in the forming of a reinforcement pattern.

* * * * *